US011083426B2

(12) United States Patent
Defreitas et al.

(10) Patent No.: US 11,083,426 B2
(45) Date of Patent: Aug. 10, 2021

(54) SPECIMEN RADIOGRAPHY SYSTEM COMPRISING CABINET AND A SPECIMEN DRAWER POSITIONABLE BY A CONTROLLER IN THE CABINET

(71) Applicant: HOLOGIC, INC., Marlborough, MA (US)

(72) Inventors: Kenneth Defreitas, Patterson, NY (US); Timothy N. Wells, Manchester, CT (US); Thomas Deyoung, Marlborough, MA (US); Henry Landry, Marlborough, MA (US); Shawn St. Pierre, Marlborough, MA (US); Shawn Hochstetler, Marlborough, MA (US); Joseph Vartolone, Marlborough, MA (US); Neil Roth, Marlborough, MA (US); Michelle Lustrino, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 5 days.

(21) Appl. No.: 16/347,570

(22) PCT Filed: Nov. 3, 2017

(86) PCT No.: PCT/US2017/060044
§ 371 (c)(1),
(2) Date: May 3, 2019

(87) PCT Pub. No.: WO2018/085719
PCT Pub. Date: May 11, 2018

(65) Prior Publication Data
US 2019/0285558 A1    Sep. 19, 2019

Related U.S. Application Data

(60) Provisional application No. 62/417,598, filed on Nov. 4, 2016.

(51) Int. Cl.
*A61B 6/00* (2006.01)
*A61B 6/04* (2006.01)
(Continued)

(52) U.S. Cl.
CPC .............. *A61B 6/4435* (2013.01); *A61B 6/04* (2013.01); *A61B 6/0407* (2013.01);
(Continued)

(58) Field of Classification Search
CPC ....... A61B 6/04; A61B 6/0407; A61B 6/0442; A61B 6/0457; A61B 6/40; A61B 6/42;
(Continued)

(56) References Cited

U.S. PATENT DOCUMENTS 6,058,159 A * 5/2000 Conway ............... G01V 5/0008
378/68
6,163,590 A * 12/2000 Wilkins .................. G21K 7/00
378/43
(Continued)

FOREIGN PATENT DOCUMENTS

WO    2012074885 A1    6/2012

OTHER PUBLICATIONS

International Search Report and Written Opinion for the International Patent Application No. PCT/US2017/060044, dated Feb. 15, 2018, 9 pages.

*Primary Examiner* — Allen C. Ho
(74) *Attorney, Agent, or Firm* — Merchant & Gould P.C.

(57) ABSTRACT

A specimen radiography system may include a controller and a cabinet. The cabinet may include an x-ray source, an x-ray detector, and a specimen drawer disposed between the x-ray source and the x-ray detector. The specimen drawer may be automatically positionable along a vertical axis between the x-ray source and the x-ray detector.

20 Claims, 13 Drawing Sheets

(51) Int. Cl.
*G01N 23/04* (2018.01)
*G21K 7/00* (2006.01)
*G01N 23/18* (2018.01)
*G01N 23/083* (2018.01)
*G01N 23/087* (2018.01)
*G01N 23/06* (2018.01)

(52) U.S. Cl.
CPC .......... *A61B 6/0442* (2013.01); *A61B 6/0487* (2020.08); *A61B 6/40* (2013.01); *A61B 6/42* (2013.01); *A61B 6/4208* (2013.01); *A61B 6/4233* (2013.01); *A61B 6/44* (2013.01); *A61B 6/4405* (2013.01); *A61B 6/4411* (2013.01); *A61B 6/4429* (2013.01); *A61B 6/4441* (2013.01); *A61B 6/4447* (2013.01); *A61B 6/4452* (2013.01); *A61B 6/508* (2013.01); *A61B 6/58* (2013.01); *A61B 6/587* (2013.01); *A61B 6/588* (2013.01); *A61B 6/589* (2013.01); *G01N 23/04* (2013.01); *G01N 23/06* (2013.01); *G01N 23/083* (2013.01); *G01N 23/087* (2013.01); *G01N 23/18* (2013.01); *G21K 7/00* (2013.01); *A61B 6/4423* (2013.01); *G01N 2223/301* (2013.01); *G01N 2223/309* (2013.01); *G01N 2223/3306* (2013.01); *G01N 2223/3307* (2013.01); *G01N 2223/6126* (2013.01)

(58) Field of Classification Search
CPC ....... A61B 6/4208; A61B 6/4233; A61B 6/44; A61B 6/4405; A61B 6/4411; A61B 6/4429; A61B 6/4435; A61B 6/4452; A61B 6/508; A61B 6/58; A61B 6/587; A61B 6/588; A61B 6/589; A61B 6/0487; A61B 6/4423; A61B 6/4441; A61B 6/4447; G01N 23/04; G01N 23/06; G01N 23/083; G01N 23/087; G01N 23/18
USPC .......... 378/51, 53–56, 58, 62, 196–198, 208
See application file for complete search history.

(56) References Cited

U.S. PATENT DOCUMENTS

| | | | | |
|---|---|---|---|---|
| 7,397,894 | B2 * | 7/2008 | Nakai | G01N 23/044 378/98.8 |
| 7,856,081 | B2 * | 12/2010 | Peschmann | G01N 23/223 378/57 |
| 7,972,062 | B2 * | 7/2011 | Nicolosi | G21K 7/00 378/205 |
| 8,038,347 | B2 * | 10/2011 | Manak | A61B 5/6887 378/189 |
| 8,050,735 | B2 * | 11/2011 | Feke | A61B 5/0059 250/336.1 |
| 8,213,570 | B2 * | 7/2012 | Panesar | G01N 23/04 378/57 |
| 8,284,896 | B2 * | 10/2012 | Singh | G01N 23/04 378/62 |
| 8,971,484 | B2 * | 3/2015 | Beckmann | G01V 5/005 378/51 |
| 8,983,030 | B2 * | 3/2015 | Ookawa | G01N 23/04 378/62 |
| 9,068,920 | B2 * | 6/2015 | Churilla | H04N 1/00795 |
| 9,129,715 | B2 * | 9/2015 | Adler | H01L 22/12 |
| 9,188,696 | B2 * | 11/2015 | Schafer | G01V 5/0016 |
| 9,234,855 | B2 * | 1/2016 | Watanabe | H05G 1/025 |
| 9,277,895 | B2 * | 3/2016 | Hara | A61B 6/0407 |
| 9,322,790 | B2 * | 4/2016 | Ookawa | G01T 7/08 |
| 9,329,139 | B2 * | 5/2016 | Itou | G01N 23/043 |
| 9,341,546 | B2 * | 5/2016 | Stuke | G01N 23/04 |
| 9,347,894 | B2 * | 5/2016 | Sims | A61B 6/508 |
| 9,492,130 | B2 * | 11/2016 | Flagle | A61B 10/0283 |
| 9,642,581 | B2 * | 5/2017 | Lowe | A61B 6/4411 |
| 9,865,424 | B2 * | 1/2018 | Ikeda | H05G 1/025 |
| 9,953,799 | B2 * | 4/2018 | Hakoda | G01N 23/02 |
| 10,008,298 | B2 * | 6/2018 | King | G21F 1/08 |
| 10,010,296 | B2 * | 7/2018 | Basu | A61B 6/588 |
| 10,098,216 | B2 * | 10/2018 | Kabumoto | G01N 23/043 |
| 10,145,806 | B2 * | 12/2018 | Tanaka | G01N 23/04 |
| 10,190,997 | B2 * | 1/2019 | Aoki | G01N 23/083 |
| 10,393,678 | B2 * | 8/2019 | Watanabe | G01N 23/083 |
| 10,488,351 | B2 * | 11/2019 | Butani | G01N 23/046 |
| 10,705,030 | B2 * | 7/2020 | Watanabe | G01N 23/046 |
| 10,809,208 | B2 * | 10/2020 | Yashima | G01N 23/04 |
| 2012/0051514 | A1 | 3/2012 | Sims et al. | |
| 2015/0131773 | A1 | 5/2015 | Lowe et al. | |

* cited by examiner

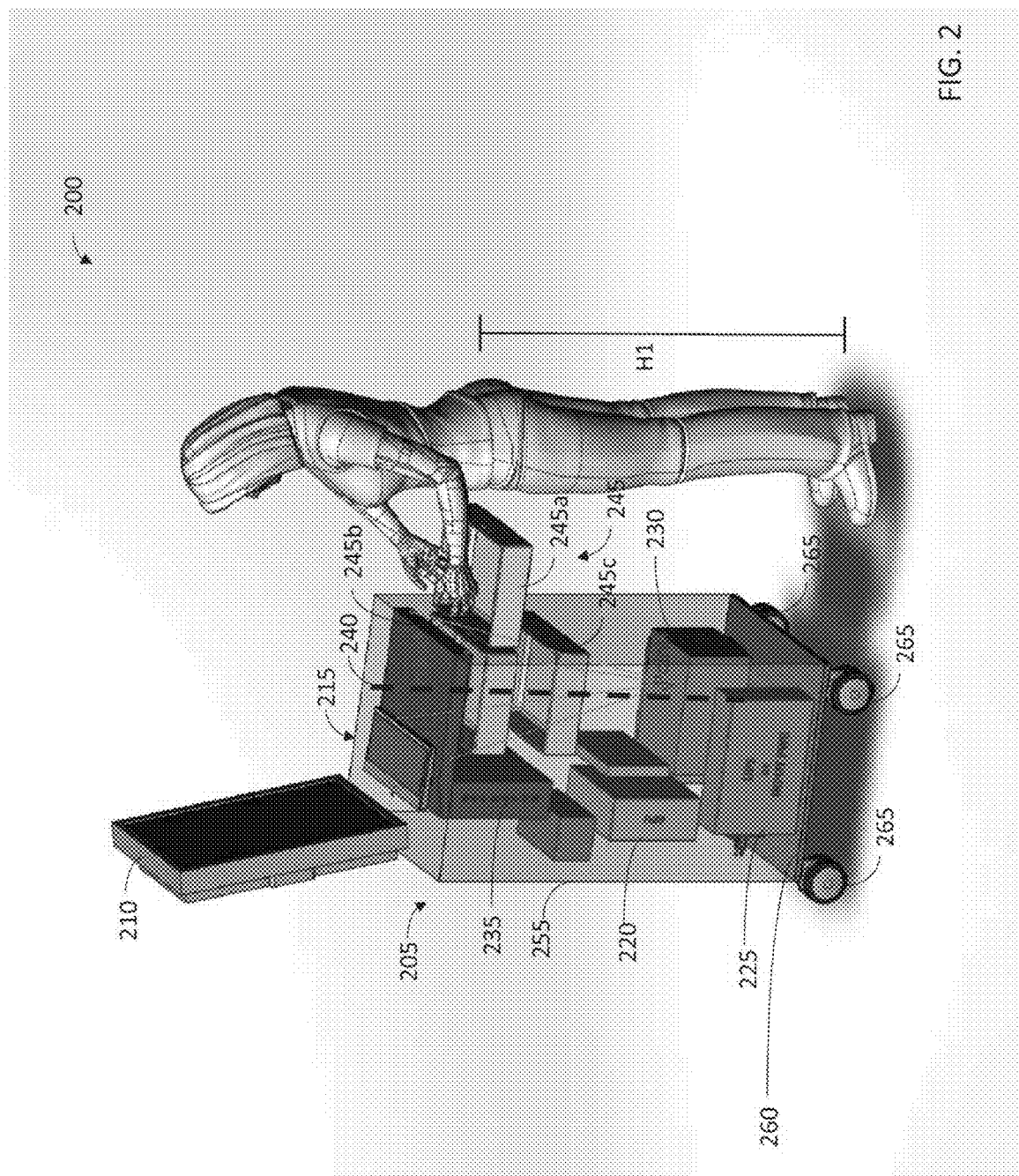

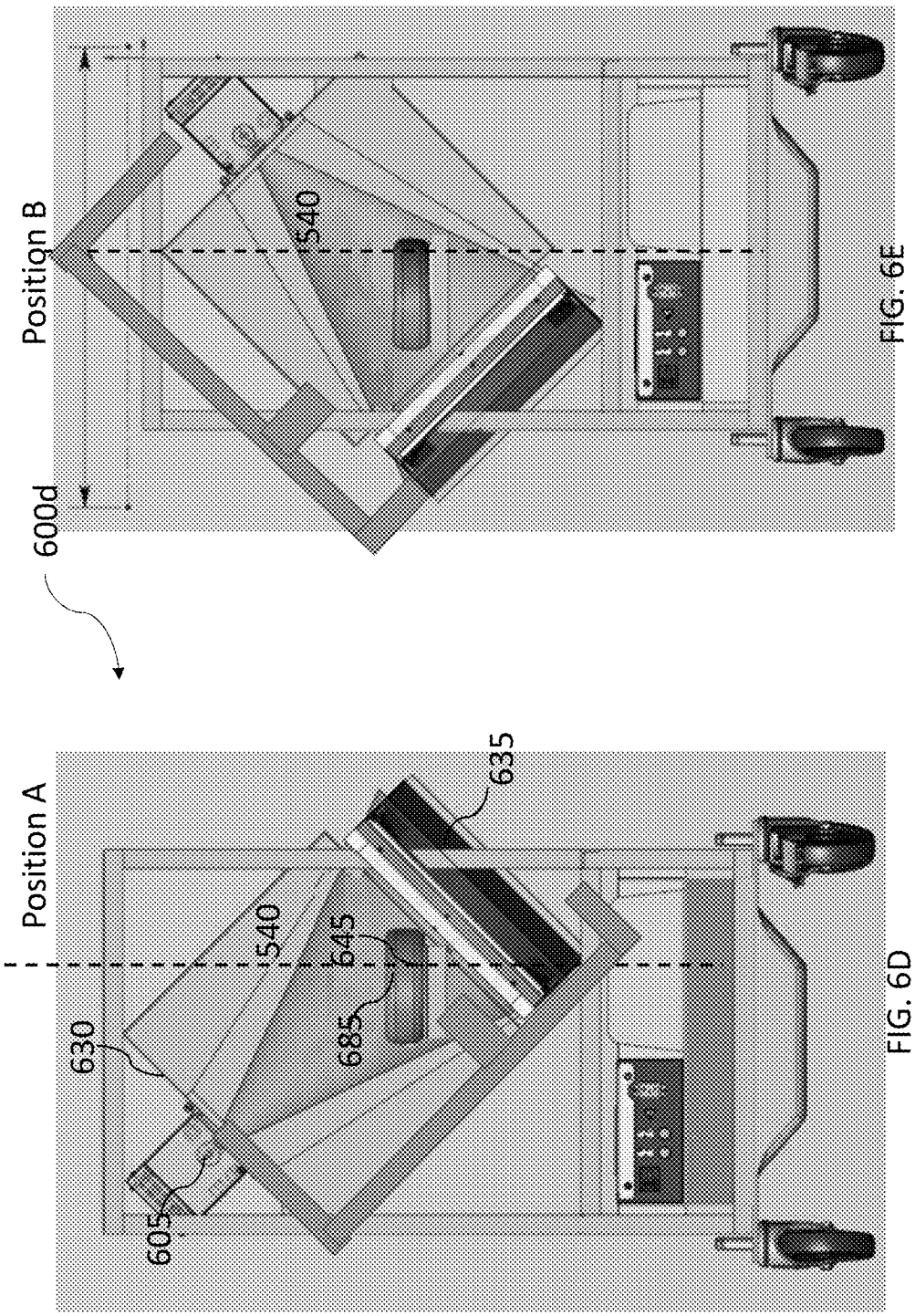

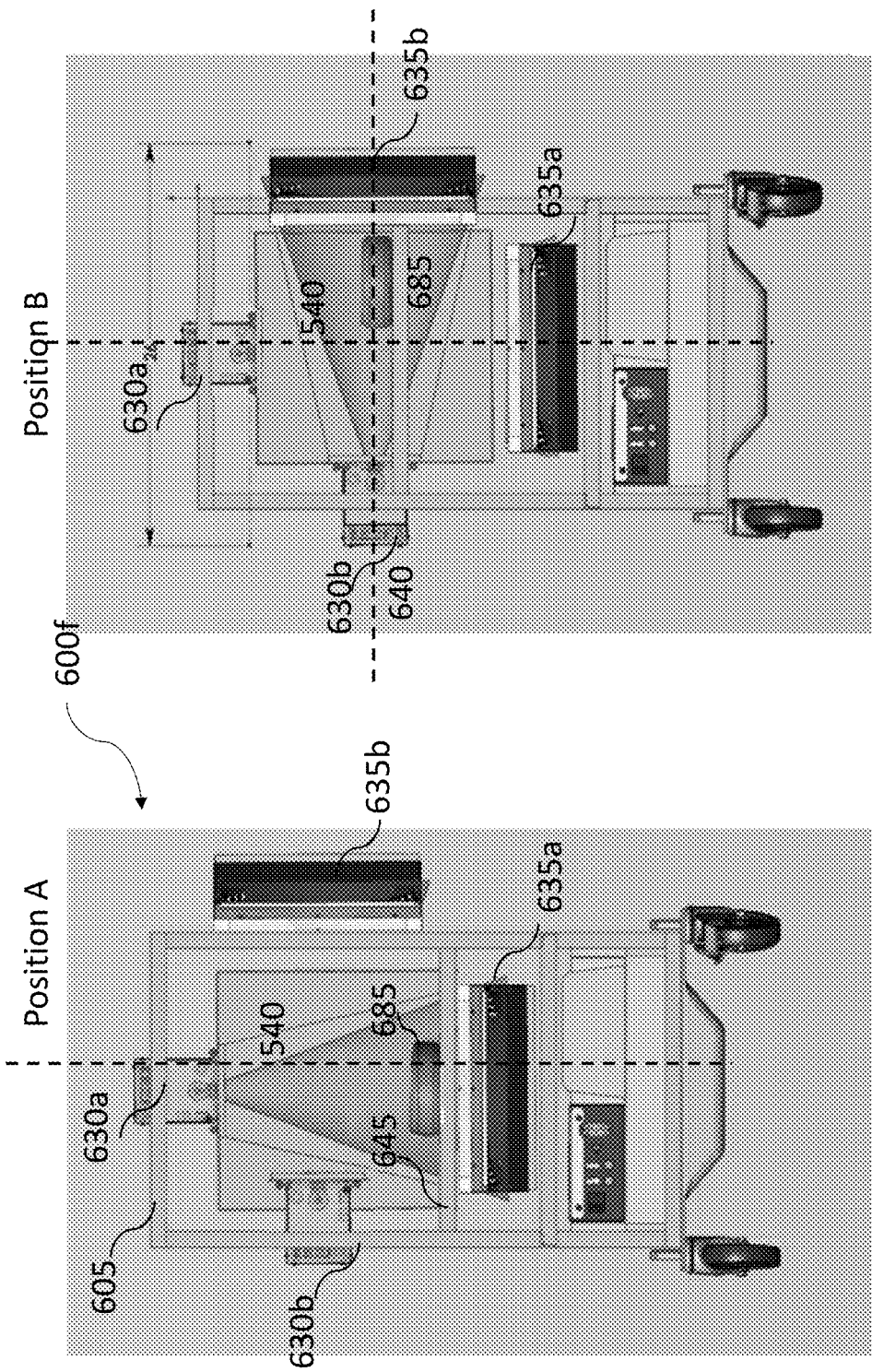

SPECIMEN RADIOGRAPHY SYSTEM COMPRISING CABINET AND A SPECIMEN DRAWER POSITIONABLE BY A CONTROLLER IN THE CABINET

CROSS-REFERENCE TO RELATED APPLICATIONS

This application is a U.S. National Phase of International Patent Application No. PCT/US2017/060044, filed Nov. 3, 2017, which claims the benefit of U.S. Provisional Patent Application No. 62/417,598, filed Nov. 4, 2016. The contents of both International Patent Application No. PCT/US2017/060044 and U.S. Provisional Patent Application No. 62/417,588 are hereby incorporated herein by reference in their respective entireties for all purposes.

FIELD OF THE DISCLOSURE

The disclosure generally relates to a specimen radiography system, and more particularly to the configuration and operation of the specimen radiography system.

BACKGROUND OF THE INVENTION

Radiography systems are used to scan tissue specimens for rapid diagnosis in medical environments such as operating rooms and clinics. Users need to be able to quickly access such systems and obtain desired images for diagnoses. Often, more than one image may be desired. In current systems, tissue specimens are manually placed and moved to particular locations in order to obtain desired magnifications and placement within the system. Such manual techniques are cumbersome, time-consuming, and prone to error (such as the specimen moving while placing it in various positions within the system). Additionally, because manual placement and movement of the specimen is required by the user, the user is typically required to reach inside the system and may be uncomfortably positioned, particularly if specimen placement is near the ground.

It is with respect to these and other considerations that the present improvements may be useful.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one aspect, the present invention comprises a specimen radiography system, comprising a controller and a cabinet operably connected to the controller. The cabinet comprises an x-ray source, an x-ray detector and a specimen drawer disposed between the x-ray source and the x-ray detector. In some embodiments, the specimen drawer is automatically positionable along a vertical axis between the x-ray source and the x-ray detector.

In one embodiment, the specimen drawer is extendable from the cabinet for receiving a specimen and the specimen drawer is rotatable. The specimen drawer can be configured to extend from the cabinet at an ergonomic position relative to a user. In another embodiment, the cabinet is portable and includes a power supply. The system can further comprise a display. In one embodiment, the specimen drawer is sealed, the specimen drawer being at least one of leak-proof, washable, and sterilizable. The specimen drawer can be formed of a generally radiolucent material. In a further embodiment, the x-ray source is disposed above the x-ray detector along the vertical axis and the x-ray detector is disposed above the x-ray source along the vertical axis. In an embodiment, the specimen drawer is configured to align with a focal point of the x-ray source.

In an embodiment, the controller is configured to at least one of automatically position and rotate the specimen drawer in response to an input received by a user interface. In addition, the specimen drawer can be configured to be extendable from and retractable within the cabinet. The specimen drawer can further include a lid.

In another aspect, the present invention comprises a method of scanning a specimen in a specimen radiography system including a controller. In certain embodiments, the method comprises the steps of extending a specimen drawer from a cabinet, placing a specimen within the extended specimen drawer, positioning the specimen drawer along a vertical axis in the cabinet, the specimen drawer movable between an x-ray source and an x-ray detector, imaging the specimen with the x-ray source and the x-ray detector; and displaying the specimen image on a display screen.

In one embodiment, the x-ray source is disposed above the x-ray detector. In another embodiment, the x-ray detector is disposed above the x-ray source. The method may further comprise receiving information via a user interface to direct the specimen drawer between the x-ray source and the x-ray detector within the cabinet. And the method may further comprise, positing the specimen drawer along the vertical axis between the x-ray source and the x-ray detector in response to a magnification setting entered by a user interface. In one embodiment, the method includes comprising rotating the specimen drawer in response to a position setting received by a user interface. In the method, the specimen drawer aligns with a focal point of the x-ray source.

In another aspect, a specimen radiography system comprises a controller, and a cabinet. The cabinet comprises an x-ray source connected to the controller, an x-ray detector disposed opposite the x-ray source which may further be connected to the controller. In cabinet further comprises a specimen drawer disposed between the x-ray source and the x-ray detector, the specimen drawer including a specimen container including a specimen excised from a patient. The specimen drawer may or may not be connected to a controller. The x-ray source, the x-ray detector, and the specimen container are positioned in a first position and image the specimen container to acquire a first image and wherein the x-ray source, the x-ray detector and the specimen container are positioned in a second position to acquire a second image, and wherein the first image and the second image are viewed on a display.

In one embodiment, the x-ray source is disposed above the x-ray detector. The x-ray source can be rotated at an angle relative to a vertical central axis of the cabinet. The specimen container can be rotated at an angle relative to the vertical central axis. The specimen container can rotated at a first angle relative to the vertical central axis and the x-ray source is rotated at a second angle relative to a vertical central axis. In one example, the first angle and the second angle are different. In one embodiment, the first position includes the specimen container rotated to a positive angle and the x-ray source rotated to a negative and the second position includes the specimen container rotated to negative angle and the x-ray source rotated to a positive angle and the x-ray detector is stationary.

In one example, the first position includes the specimen container rotated to positive 15 degrees and the x-ray source rotated to negative 30 degrees and the second position includes the specimen container rotated to negative 15 degrees and the x-ray source rotated to positive 30 degrees.

In another embodiment, the x-ray source and the x-ray detector are both rotated relative to a vertical axis central of the cabinet. In one example, the first position includes the x-ray source rotated to a negative angle and the second position includes the x-ray source rotated to a positive angle and the specimen container remains stationary. The first position may include the x-ray source rotated to negative 45 degrees and the second position includes the x-ray source rotated to positive 45 degrees.

In another embodiment, the first position includes the x-ray source rotated to a negative angle and the second position includes the x-ray source rotated to a positive angle and the specimen container remains stationary. In one example, the first position includes the x-ray source rotated to negative 45 degrees and the second position includes the x-ray source rotated to positive 45 degrees.

In another embodiment, the first position includes the x-ray source rotated to a zero angle and the second position includes the x-ray source rotated to a 90 degree angle and the specimen container remains stationary. In one example, the first position includes the x-ray source rotated to a zero angle and the second position includes the x-ray source rotated to a 90 degree angle and the specimen container moves horizontally toward the x-ray detector.

In another embodiment, the system further comprises a second x-ray source and a second x-ray detector. In one example, the second x-ray source is disposed orthogonal to the first x-ray source and the second x-ray detector is disposed orthogonal to the first x-ray detector. In one example, the first position includes the specimen container placed centrally between the first and second x-ray detectors and the first and second x-ray sources. The second position may include the specimen container moved along a horizontal axis to be proximal to the second detector.

In another aspect, a method of scanning a specimen in a specimen radiography system is disclosed. The method comprises the steps of imaging the specimen with the x-ray source and the x-ray detector at a first position and storing a first image, imaging the specimen with the x-ray source and the x-ray detector at a second position and storing a second image, processing the first and the second image, and displaying the first and second specimen image on a display screen.

BRIEF DESCRIPTION OF THE DRAWINGS

By way of example, one or more embodiments of the disclosed device will now be described, with reference to the accompanying drawings, in which:

FIG. 2 illustrates a perspective view of a specimen radiography system according to an embodiment of the present invention.

FIGS. 6D and 6E illustrate a perspective view of a cabinet of a specimen radiography system according to another embodiment of the present invention.

FIGS. 6F and 6G illustrate a perspective view of a cabinet of a specimen radiography system according to another embodiment of the present invention.

DETAILED DESCRIPTION

Figure 1:
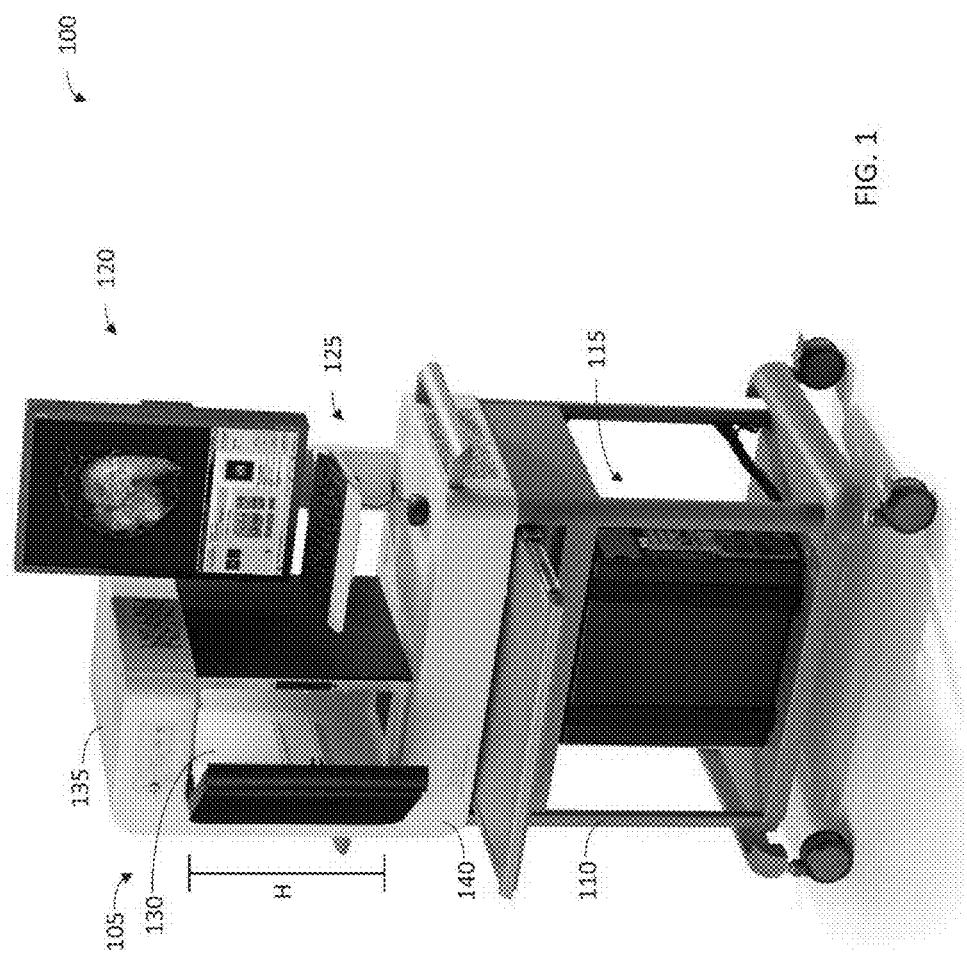
FIG. 1 illustrates a perspective view of an existing specimen radiography system.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Referring to FIG. 1, an existing specimen radiography system 100 is shown. A cabinet 105 may be disposed on a portable stand 110. The specimen radiography system 100 may further include a controller 115, a non-transitory storage medium, a processor, a display 120 and user interface 125, e.g., a computer keyboard and/or mouse, or other information entry devices operably connected to each other. In embodiments, the controller 115 may be separate from the cabinet 105.

The cabinet 105 may be configured for scanning tissue specimens, e.g., by radiography. A specimen may be manually placed in an enclosed space 130 of the cabinet 105 for scanning. The enclosed space 130 may have adjustable shelves or other manual placement means for disposing the specimen at a different height H in the cabinet 105. The placement of the specimen in the enclosed space 130 of the cabinet 105 is related to a magnification of the image shown on the display 120, in that an x-ray source 135 and an x-ray detector 140 are disposed at opposite ends of the cabinet 105. A user may scan the specimen at a first magnification by placing the specimen at a selected height H in the enclosed space 130 of the cabinet 105. If the user desires to adjust the magnification of the scanned specimen, the user must manually adjust the height H of the specimen within the cabinet 105 before scanning. This results in additional time needed to acquire desired images, and manual adjustment of the specimen between each scan. The user must also bend to the level of the cabinet 105 to properly adjust the specimen in between scans, and the cabinet 105 on the stand 110 may result in a top-heavy system.

Referring now to FIG. 2, a radiography scanning system 200 according to an embodiment of the present invention is shown. The radiography scanning system 200 may include a cabinet 205, with an x-ray source 230 and an x-ray detector 235. The x-ray detector 235 may be disposed vertically above the x-ray source 230. In an embodiment, the x-ray detector 235 is disposed at a top of the cabinet 205, and the x-ray source 230 is disposed at a base 260 of the cabinet 205. It is advantageous to place the x-ray source 230 lower in the cabinet 205 to provide stability of the cabinet 205, by lowering the center of gravity. It is also envisioned that the x-ray source 230 may be disposed vertically above the x-ray detector 235, as shown in the radiography scanning system 300 of FIG. 3. It is advantageous to position the x-ray source 230 above the x-ray detector 235 from producing clearer images. Placement of the x-ray source 230 and the x-ray detector 235 may interact with other cabinet components, e.g., the controller 220 and the power supply 225. In order to minimize interferences with these components, shielding these other cabinet components from the x-ray detector 235 and/or the x-ray source 230 may be necessary. It should also be understood that altering the position of the x-ray source 230 and the x-ray detector 235 may result in other cabinet components also being located in different areas of the cabinet 205. In any configuration, the x-ray source 230 and the x-ray detector 235 are aligned along a vertical axis 240, so that the x-ray detector 235 may receive x-rays from the x-ray source 230.

The radiography scanning system 200 may further include a display 210, a user interface 215, a controller 220, and a power supply 225 operably connected to each other. In an embodiment, the controller 220 and the power supply 225 may be enclosed within a housing 255 of the cabinet 205. In an embodiment the controller 220 and/or power supply 225 may be disposed at the base 260 of the cabinet 205. The cabinet 205 may include protection of the controller 220 and the power supply 225 from radiation of the x-ray source 230. In an embodiment, the cabinet 205 may be portable. For example, the cabinet 205 may include wheels 265.

A specimen drawer 245 may be included in the cabinet 205. The cabinet 205 may be configured for the specimen drawer 245 to extend from and retract into the cabinet 205 for user access. In an extended state, illustrated at 245a, a user may deposit, retrieve, and/or adjust a specimen in the specimen drawer 245. In an embodiment, the specimen drawer 245 may be extendable and/or retractable at a position in the cabinet 205 at an average user height H1 from the base 260 and/or the wheels 265. This allows the user to handle the specimen relative to the specimen drawer 245 in an ergonomic manner. That is, the user does not have to uncomfortably bend and/or reach to access the specimen, improving user accessibility and comfort, and reducing potential musculoskeletal injury to the user from operating the specimen radiography system 200.

Figure 2A:
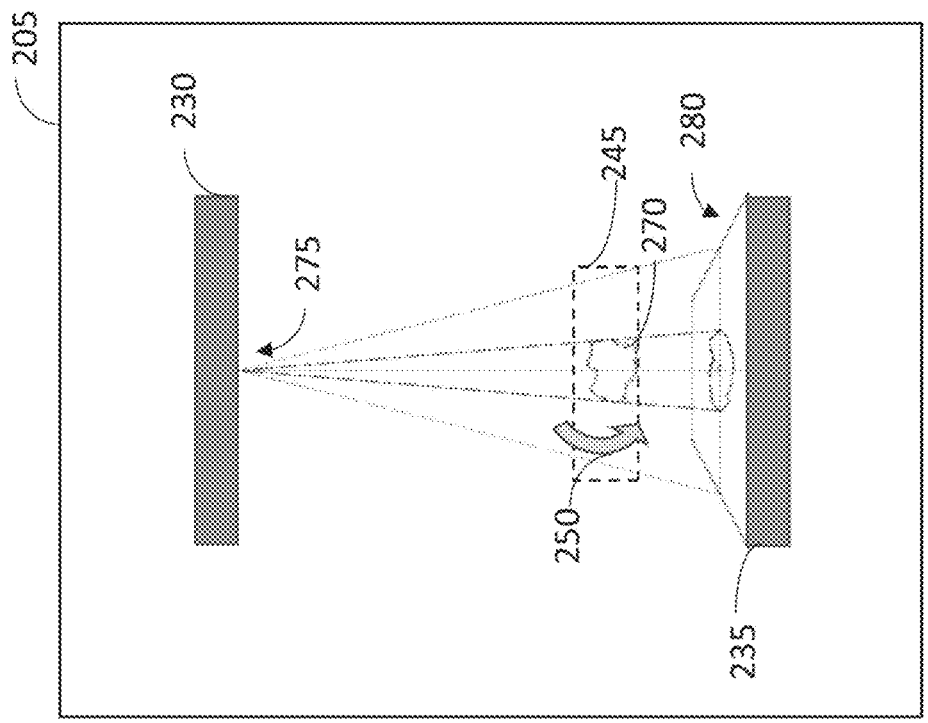
FIG. 2A illustrate a front view of a portion of the specimen radiography system according to an embodiment of the present invention.
Figure 3:
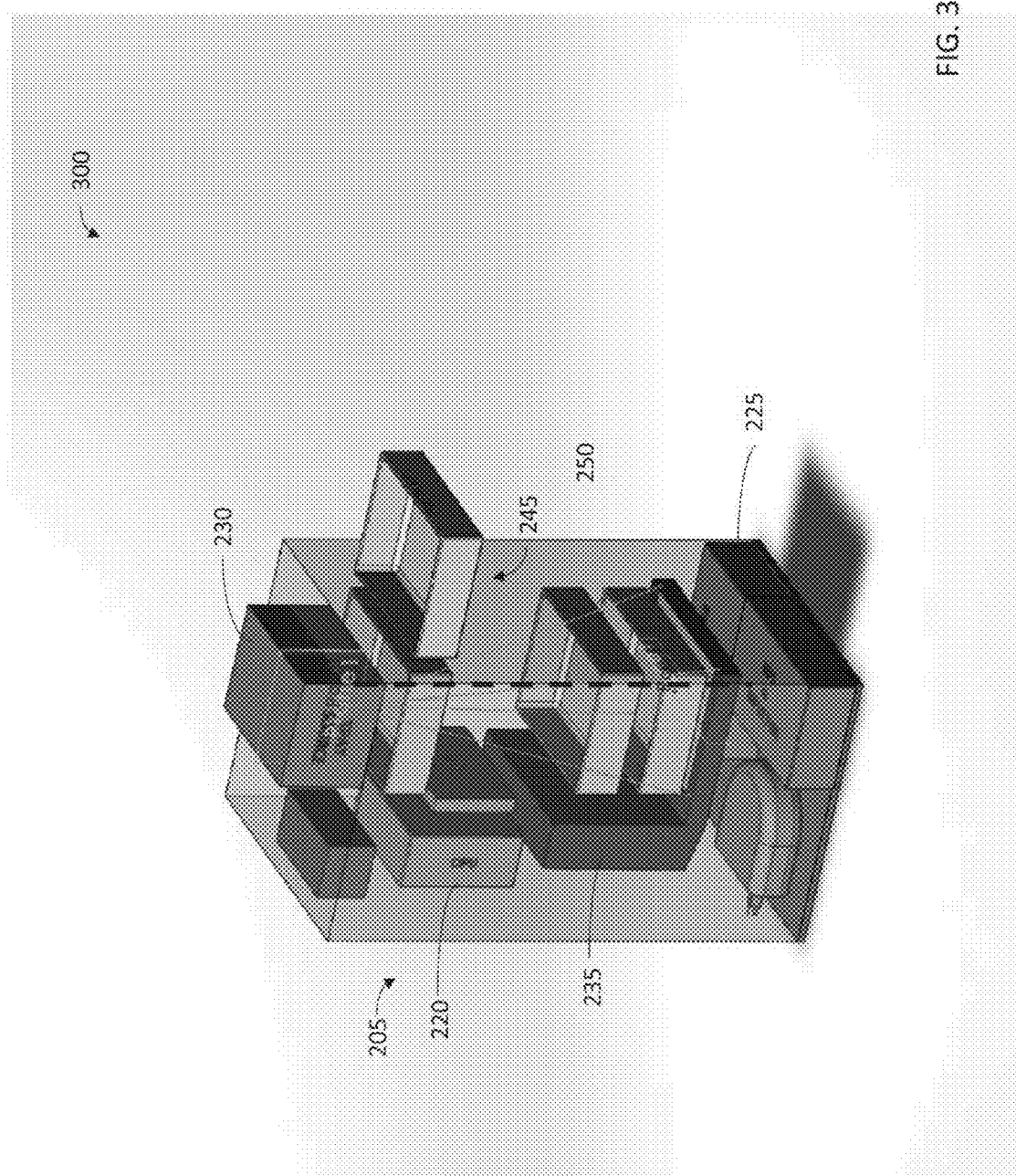
FIG. 3 illustrates a perspective view of a cabinet of a specimen radiography system according to another embodiment of the present invention.

In the retracted state, illustrated at 245b, the specimen drawer 245 is brought into alignment along the vertical axis 240. The specimen drawer 245 may be movable between the x-ray source 230 and the x-ray detector 235 along the vertical axis 240, as illustrated at 245c. The specimen drawer 245 may be movable in a downward vertical motion to sit atop the x-ray source 230 or the x-ray detector 235 at the base 260 of the cabinet 205. For example, as shown in FIG. 2A, a tissue specimen 270 may be disposed between a focal point 275 of the x-ray source 230 and an image plane 280 of the x-ray detector 235. The specimen drawer 245 may be automatically positioned between the x-ray source 230 and the x-ray detector 235, so that a tissue specimen 270 is rotatable in a direction shown by arrow 250 to produce orthogonal views and/or multiple projections. This is advantageous because from these additional rotated views, a three-dimensional (3D) data set of the tissue specimen may be generated. It should be understood that although the x-ray source 230 may be disposed above the x-ray detector 235, in some embodiments the x-ray detector 235 may be disposed above the x-ray source 230.

The specimen drawer 245 may be rectangular, or any shape configured to be extendable from and movable within the cabinet 205. In embodiments, the specimen drawer 245 may be circular, cylindrical, or conical. The specimen drawer 245 may have a depth so that a tissue specimen 270 is contained within the specimen drawer 245, thereby preventing leakage in the cabinet 205 and/or contamination of the tissue specimen 270. In an embodiment, the specimen drawer 245 may include a lid.

The specimen drawer 245 may be configured out of a material that x-rays may pass through, e.g., a carbon fiber material and/or other generally radiolucent material. The specimen drawer 245 may be configured to be leak-proof, washable, and/or sterilizable so that it may be easily cleanable between specimen samples without having to clean the entire interior of the cabinet 205, thereby reducing the time needed for the scanning operation and increasing user efficiency.

The controller 220 may automatically control the position of the specimen drawer 245 relative to the x-ray source 230 and the x-ray detector 235, receiving information by a user from the user interface 215. For example, the user may desire a series of images of a scanned tissue specimen 270. The controller 220 may direct the specimen drawer 245 to the desired positions along the vertical axis 240 between the x-ray source 230 and the x-ray detector 235, without the user having to manually move the tissue specimen 270. This automatic control of the position of the specimen drawer 245 allows the user to receive the desired images in a repeatable manner without having to manually adjust the tissue specimen 270. Time needed for scanning a tissue specimen 270 is also reduced because the specimen drawer 245 may be driven to the position(s) immediately without user interference. Alternatively, in response to user input or preset settings, the specimen drawer 245 may be automatically positioned for various views including various magnification views. One or more sensors may optionally be used to ensure that the central vertical axis 240 of the specimen drawer 245 is aligned with the focal point 275 of the x-ray source 230 (FIG. 2A). Alternatively, user input or preset settings may shift the specimen drawer 245 such that the tissue specimen 270 is always positioned generally about the focal point 275.

The cabinet 205 may include known positioning mechanisms for moving and positioning the specimen drawer 245, including but not limited to tracks, conveyors, and/or pulley mechanisms. The positioning mechanisms may be controllable by the controller 220, and include sensors or other detection means for determining the position of the specimen drawer 245 relative to the x-ray source 230 and the x-ray detector 235. The controller 220 may relate the relative position of the specimen drawer 245 to the x-ray source 230 and/or the x-ray detector 235 to a desired magnification of an image of the tissue specimen 270.

The housing 255 of the cabinet 205 may include an opening for the specimen drawer 245 to extend from, for user access. The opening may be a cut-out of the housing 255, and may include a cover, or door. The door may be sealable so that radiation is contained within the cabinet 205.

The door may have a locking mechanism so that the door cannot be opened during scanning to ensure user safety.

In operation, a user may operate the radiography scanning system 200 via the user interface 215. For example, the controller 220 may direct the specimen drawer 245 to extend from the cabinet 205. Once in the extended position 245a, the user may place a tissue specimen 270 in the specimen drawer 245 and direct the specimen drawer 245 to retract within the cabinet 205. In an embodiment, a sensor may detect the tissue specimen 270 and retract in response to the sensor. For example, the sensor may be a vision and/or weight sensor to detect presence of the tissue specimen 270.

The specimen drawer 245 including the tissue specimen 270 may be retractable within the cabinet 205. For example, the controller 220 may control the specimen drawer 245 to eject from an opening of the cabinet 205 to receive a tissue specimen 270, and retract back into the cabinet 205. The specimen drawer 245 may then be aligned along the vertical axis 240, so that the specimen drawer 245 is aligned between the x-ray source 230 and the x-ray detector 235. For example, the controller 220 may automatically align vertical axes of the specimen drawer 245 with the focal point 275 of the x-ray source 230 so that the tissue specimen 270 is aligned with the focal point 275 (FIG. 2A). One or more sensors may detect the tissue specimen 270 with respect to the focal point 275 to ensure proper alignment. In some embodiments, the controller 220 may disable imaging unless and until the vertical axes of the specimen drawer 245 are properly aligned with the x-ray source 230 and the x-ray detector 235. This may be advantageous to increase the quality and repeatability of the imaging.

The radiography scanning system 200 may scan the tissue specimen 270 and the specimen drawer 245, by the controller 220 generating signals to the x-ray source 230 and the x-ray detector 235. The specimen drawer 245 may be scanned in one or more positions along the vertical axis 240. The scanned image of the tissue specimen 270 is a function of the position of the specimen drawer 245 along the vertical axis 240. For example, a distance from the x-ray detector 235 to the specimen drawer 245 relates to a magnification of the tissue specimen 270 in the scanned image.

One or more positions for the specimen drawer 245 along the vertical axis 240 may be pre-programmed in the controller 220 to receive a pre-selected set of magnifications of the tissue specimen 270, which may be stored in a memory of the controller 220. A user may select the pre-programmed positions, and/or may enter desired magnifications of images.

The specimen drawer 245 is then moved to a desired location, e.g., shown at 245c. The x-ray source 230 may then send x-rays to the x-ray detector 235, capturing an image of the tissue specimen 270 disposed between. The image may then be shown on the display 210, and/or stored in the memory of the controller 220.

Figure 4:
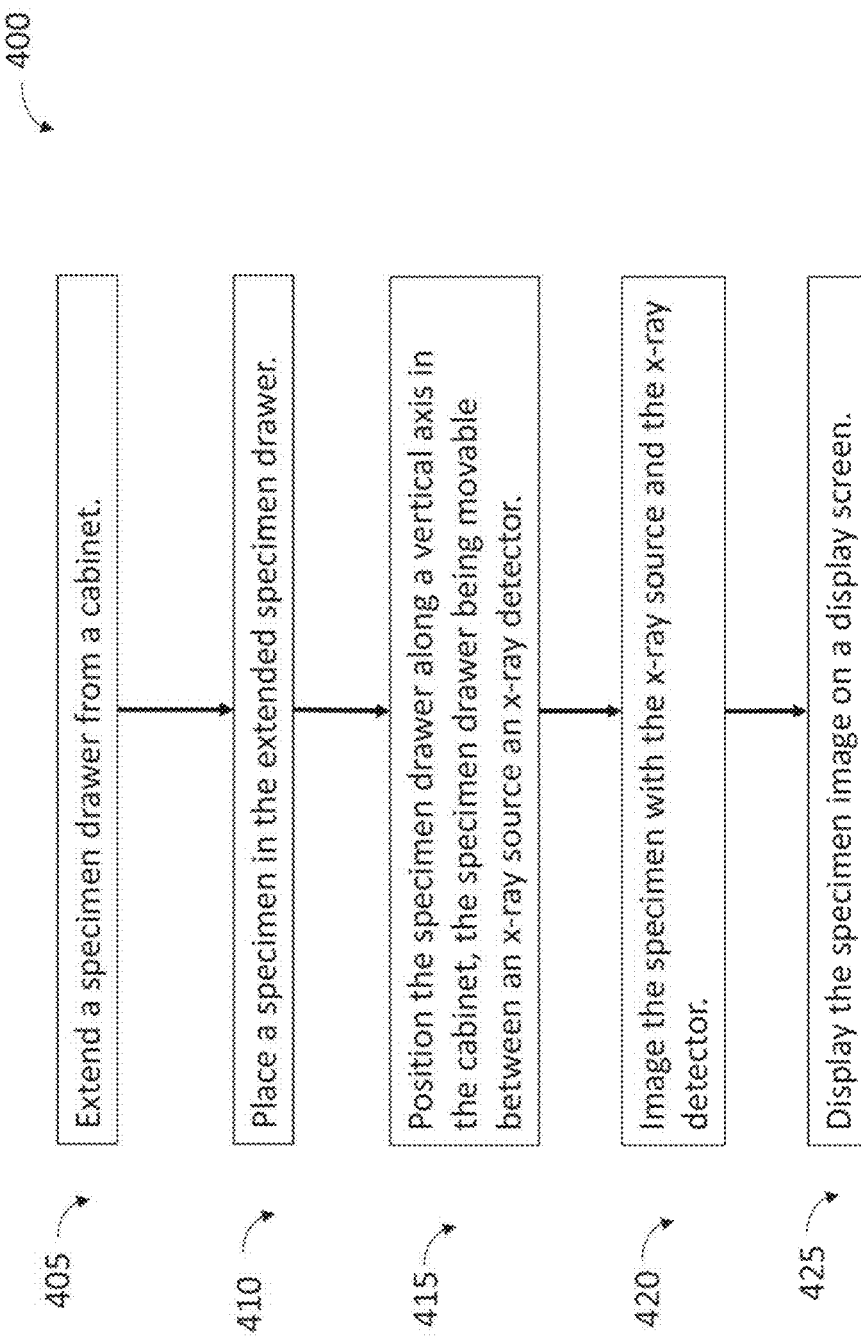
FIG. 4 illustrates a flow diagram of a method of scanning a specimen in a specimen radiography system according to an embodiment of the present invention.

Referring now to FIG. 4, a flow diagram 400 of a method of scanning a specimen in a specimen radiography system is shown. At step 405, the specimen drawer is extended from a cabinet of the specimen radiography system. The controller may direct specimen drawer, from a program stored in a memory of the controller, from user input, or a combination thereof. At step 410, the user may place the specimen in the extended specimen drawer. At step 415, the specimen drawer is positioned along a vertical axis in the cabinet. The specimen drawer is movable between an x-ray source and an x-ray detector. At step 420, the specimen is imaged with the x-ray source and the x-ray detector, and at step 425, the image of the specimen is shown on a display screen.

Figure 5B:
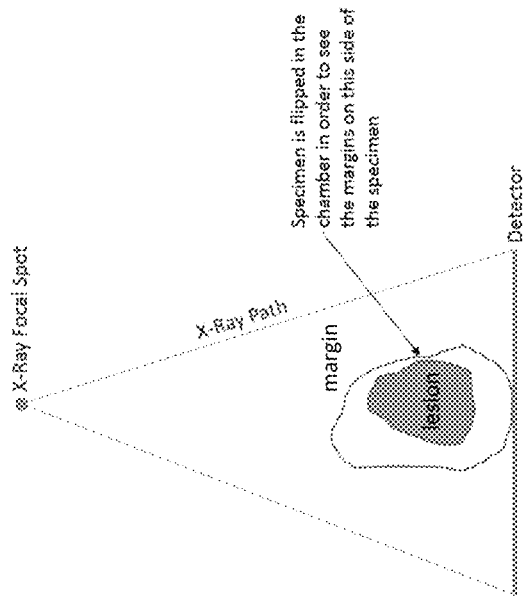
FIGS. 5A and 5B illustrate the specimen within a traditional specimen radiography system.
Figure 5A:
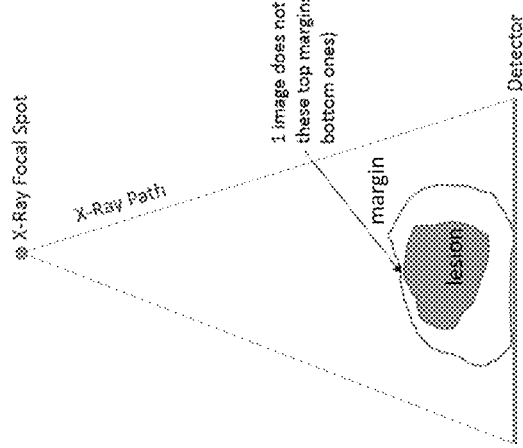

A specimen radiography system is often used in the operating room to verify that the entire lesion was removed during a lumpectomy. These specimen are often large, and are sometimes comprised of dense tissue. In addition, if the lesion is comprised of dense tissue, a traditional specimen radiography system may not properly determine if the specimen includes cancerous tissue. An example of a specimen is shown in FIGS. 5A and 5B where the specimen is shown to have a lesion in the center that is surrounded by margin. It is very important to be able to properly assess that the entire lesion was removed by determining whether the margins of the lesion are clear. The surgeon wants to minimize the removal of healthy tissue while removing the entire lesion. To make sure the margins are clear in a three-dimensional specimen the entirety of the perimeter would need to be images. Traditional specimen containers suffer from the shortcomings of specimens being distorted in the viewing tray, for example, because traditional specimen containers may compress the specimen. If the specimen is compressed, it could damage or thin out the specimen and can artificially expand the margins of the specimen. Other short comings include that the surgeon must manually manipulate the specimen container by turning the specimen container to capture multiple images and make sure that the entirely of the lesion is removed (FIG. 5B). This takes time and by moving the specimen holder margins to an orthogonal position the specimen could be distorted and the surgeon would not be able to properly assess whether the entire lesion is removed. Therefore, a system that overcomes such shortcomings is desired.

In the embodiments of FIGS. 5C-6G, there are included multiple methods and mechanisms for obtaining omni directional views of the specimen. That is these systems allow for viewing of the specimen from a larger portion of the perimeter without distorting the specimen, by for example, moving both the specimen container and the x-ray source relative to each other, moving the x-ray source and the x-ray detector relative to the specimen or including multiple detectors and sources.

Figure 5D:
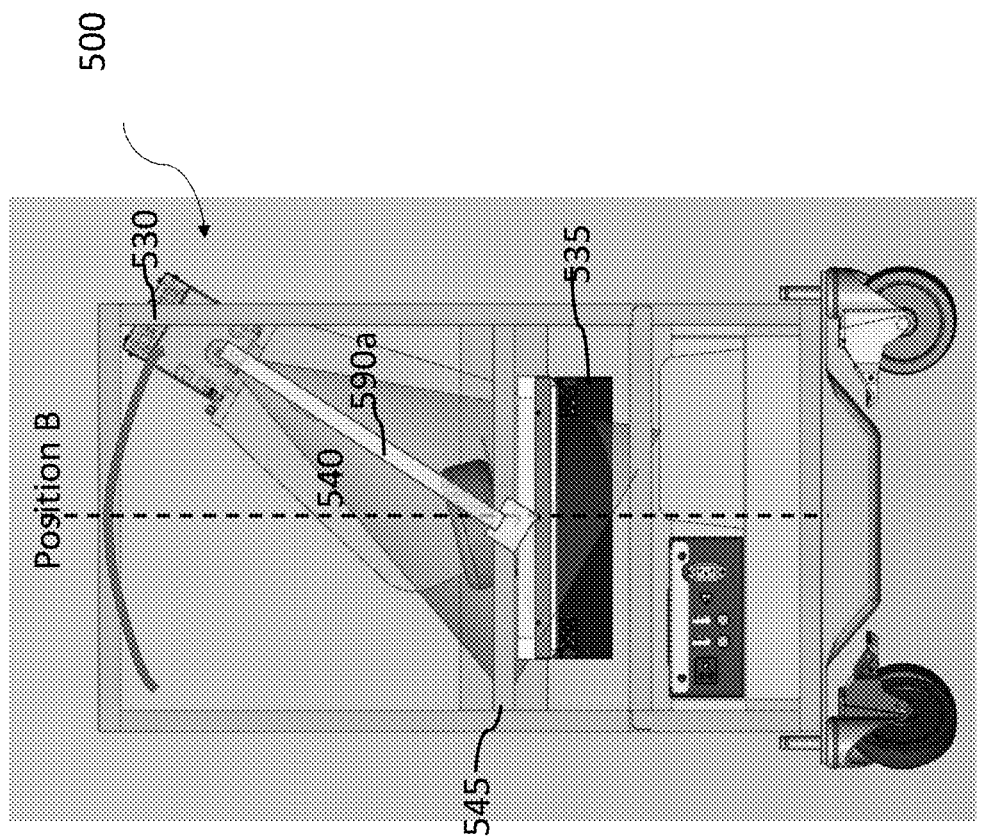
FIGS. 5C and 5D illustrate a perspective view of a cabinet of a specimen radiography system according to another embodiment of the present invention.
Figure 5C:
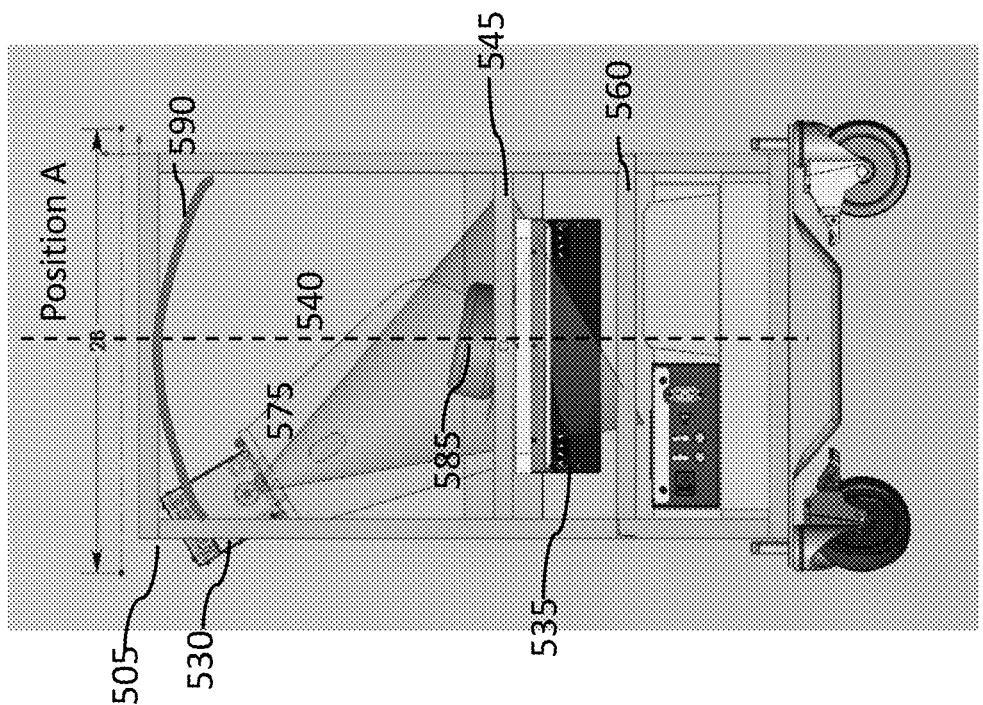

Referring now to FIGS. 5C and 5D, a radiography scanning system 500 according to another embodiment of the present invention is shown. The system 500 may include a cabinet 505, with an x-ray source 530 and an x-ray detector 535. The x-ray detector 535 may be disposed below the x-ray source 530. In an embodiment, the x-ray source 530 is disposed at a top of the cabinet 505, and the x-ray detector 535 is disposed at a base 560 of the cabinet. In one example implementation, the size of the cabinet is approximately 29"×25".

The x-ray source 530 and the x-ray detector 535 are aligned along a vertical axis 540, so that the x-ray detector 535 may receive x-rays from the x-ray source 530 that travel through the specimen container 585. In one example, the detector is a HDT detector.

Similarly to system 200, a specimen drawer 545 may be included in the cabinet 505. A user may deposit, retrieve, and/or adjust a specimen container 585 in the specimen drawer 545. The specimen container 585 includes one or more samples collected by a user and placed into the container 585 after the specimens are excised from the patient. The specimen drawer 545 and the specimen container 585 may include connection or contact point or mechanisms that allow the specimen container 585 to attached to the drawer 545. For example, the bottom of the specimen container 585 and the top of the drawer 545 may include a snap fit design, having a male connection on the drawer 545 and a female counterpart on the container 585. Other methods of connection are contemplated are within the scope of this application.

The specimen drawer is capable of being tilted while the specimen container is connected to it with respect to the vertical axis 540 and the housing and base 560 of the cabinet 502. It is contemplated that the entire drawer can be titled or alternatively a portion of the drawer can be titled. To tilt the drawer, many mechanisms can be implemented. For example, an electro-mechanical system or a hydraulic system can be implemented that is actuated and controlled by a controller. The tilting mechanism can for example include two cross-bars that are disposed under the specimen drawer and which are alternatively extended and lowered. The rotation or the title of the specimen drawer is at a central point, the drawer and the specimen container does not translate along a horizontal axis in line with the top of the detector.

Figure 5F:
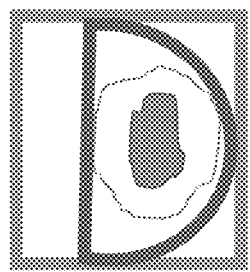
FIGS. 5E and 5F illustrate a view of the specimen container within a specimen radiography system according to some embodiments of the present invention.
Figure 5E:
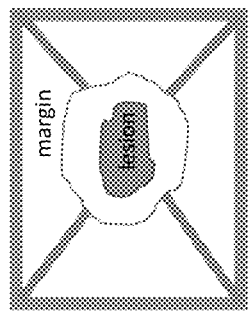

Mechanisms for holding the specimen in place inside the specimen container are also contemplated. FIGS. 5E-5F show some examples of specimen containers 585. In FIG. 5E, the specimen is held by multiple attachment arms that extend diagonally from the corners of the container to the center of the container. The specimen is located at the center of the specimen container 585 and is held in place at the center using the attachment arms. In FIG. 5F a cup is shown that hold the specimen in place. The cup could be made from a foam material that resists movement of the specimen. In all embodiments, the specimen container is made of radiolucent material that does not create artifacts when imaged using the x-ray source and x-ray detector. Other mechanisms for holding the specimen in place are contemplated, including mesh materials, rings, tape, hammock type construction, and tube-like constructions as well as other methods which are within the scope of this disclosure.

The x-ray source 530 is also rotated between position A shown in FIG. 5AC and position B in FIG. 5D. Position A is at an angle with reference to the vertical axis 540. In one example, a radial guide track 590 could be used to allow the x-ray source 530 to travels along the radial guide track 590 from position A to position B. The x-ray source 530 can then be rotated into any number of positions and angles along the path of the radial guide track 590. In one example, a stepper motor and drive belt could be used to move the x-ray source along the path. In another embodiment, the x-ray source is connected to a single elongated arm 590a. The elongated arm is centrally pivoted and the x-ray source is rotated in an arc around a central pivot point. Alternatively, the x-ray source can be linearly translated along the length of the cabinet top having a linear conveyer like translation mechanism and a portion of the x-ray source can then be tilted at an angle once it reaches the desired position. In examples the path or the arc of rotation of the x-ray source may span anywhere from positive 90 degrees about the target to negative 90 degrees (with 0 degrees being aligned with the vertical axis 540 and +/−90 degrees orthogonal to the vertical axis 540).

The specimen drawer 545 and/or the specimen container 585, and the x-ray source 530 can be connected to the controller for control the movement of the specimen drawer 545 and/or the specimen container 585, and the x-ray source 530. In one example, the control of the specimen drawer 545 and/or the specimen container 585, and the x-ray source 530 can be controlled via the arm assembly and/or the tilting mechanism as described above. Both the arm assembly and/or the tilting mechanism may include a motor that translates a signal from the controller into motion of the arm assembly and/or the tilting mechanism.

In one embodiment, the specimen drawer 545 is tilted into a direction opposite the rotation of the x-ray source 530, with respect to the vertical axis 540, the specimen drawer facing away from the source. For example, if the specimen drawer 545 is rotated in the positive direction, the x-ray source 530 is rotated into the negative direction as shown in Position A. Similarly, if the specimen drawer 545 is rotated in the negative direction, the x-ray source 530 is rotated into the positive direction as shown in Position B. The x-ray source 530 can activated for a particular exposure time as the x-ray source 530 moves into the imaging position A, and exposure is repeated with the imaging position B, a total cycle period lasting seconds. After each exposure the x-ray source 530 is deactivated. In each of the imaging positions A and B, the contents of the x-ray detector are read out and stored.

In one example of use of the system, the specimen drawer 545, including the specimen container 585, is movable +/−15° in a plane in reference to the vertical axis 540 and the x-ray source is rotated +/−30° in a plane in reference to the vertical axis 540 and in reference to the specimen drawer and container. In one example, the x-ray source 530 is rotated +30 deg and the specimen drawer is rotated −15 deg and an image is taken. Then the x-ray source 530 is rotated −30 deg and the specimen drawer 545 is rotated +15 deg and another image is taken. The resultant images taken of the specimen would be +45 deg and −45 deg. In this embodiment, the x-ray detector 535 is stationary and is not moved while both the specimen drawer 545 and the x-ray source 530 are rotated. By keeping the x-ray detector 535 stationary greater image quality can be achieved. Any other angles of rotation for both the specimen container and the x-ray source are contemplated.

The images taken at position A and position B are then the viewed side by side on the display. By taking more than one image at different angles, more information about the specimen can be obtained. For example, slices advantageously reduce or eliminate problems caused by tissue overlap and structure noise in two-dimensional mammography imaging Various imaging algorithms may additional be used to reduce distortion and clean up the resultant images.

It is appreciated by the inventors, that in order to obtain optimal image quality, the specimen inside the specimen container should remain stationary. Any change to the specimen inside the specimen container could result in imaging artifacts, including blurring of the image. Large specimens, such as those excised as a result of a lumpectomy, may be particularly at risk of moving during imaging while the specimen container is being moved. The density or thickness of the specimen can be obtained by using ultrasound and imaging the specimen in the specimen container prior to taking the images at various positions, including Position A and Position B. Based on the determination of the thickness, the controller can then control the angle of rotation of both the x-ray source and the specimen drawer. In one example implementation, if the specimen is over a threshold of a particular thickness, the rotation angles are lowered in order to minimize specimen movement. In another example implementation, a table of multiple thicknesses corresponds to particular angles of rotation, with larger angles for thinner samples and smaller angles corresponding to larger samples.

Figure 6B:
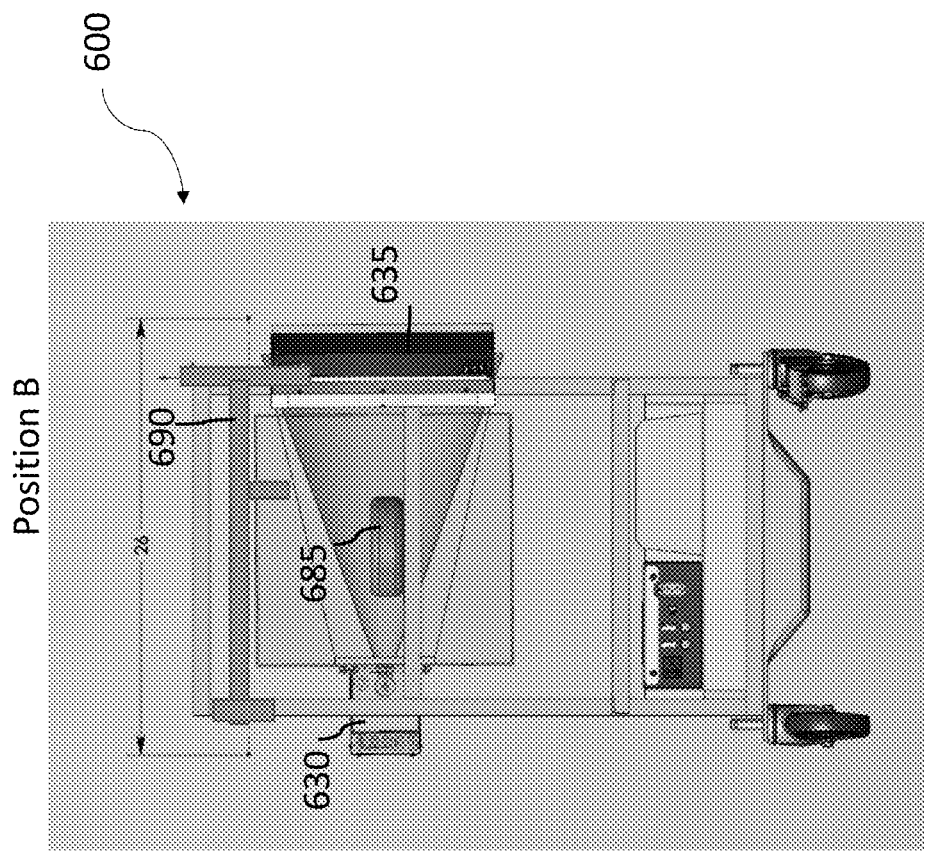
FIGS. 6A-6C illustrate a perspective view of a cabinet of a specimen radiography system according to another embodiment of the present invention.
Figure 6A:
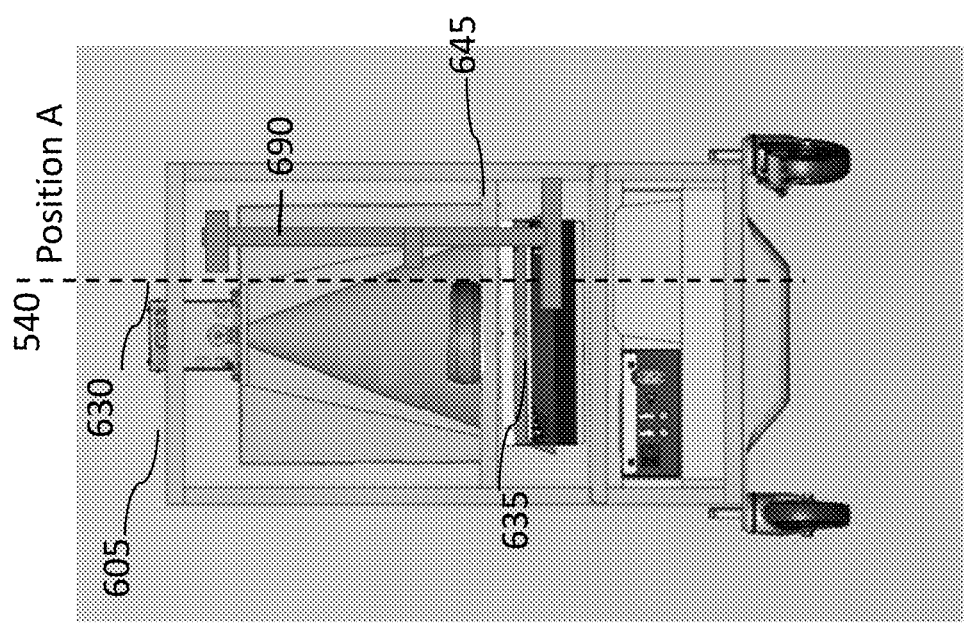
Figure 6C:
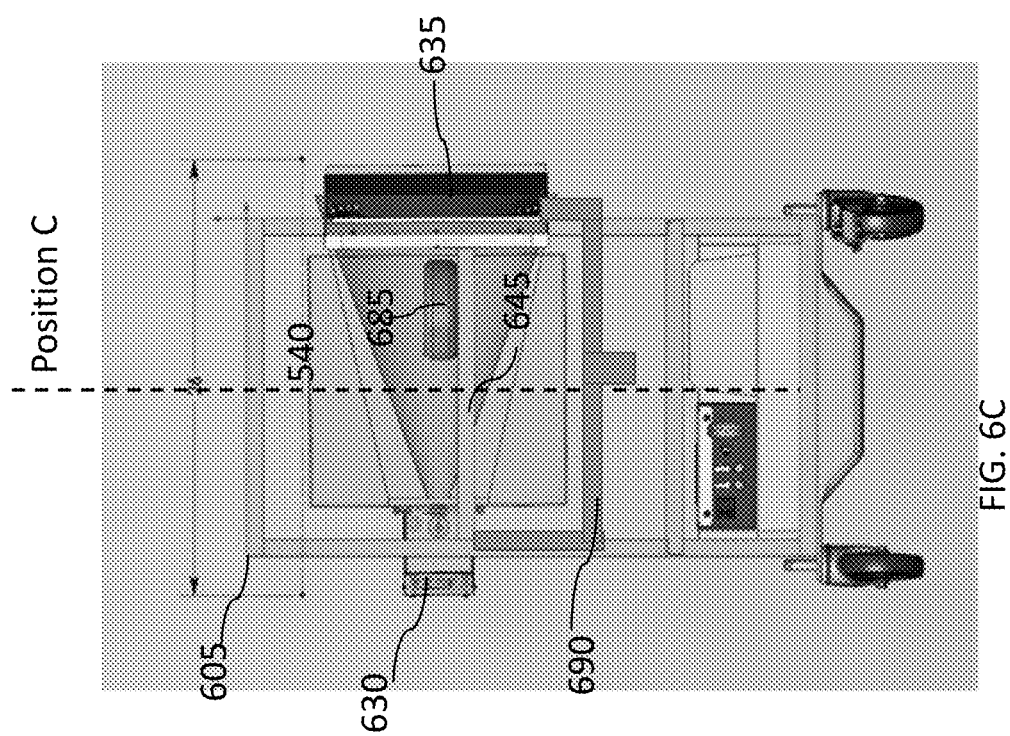

Referring now to FIGS. 6A-6C, a radiography scanning system 600 according to another embodiment of the present invention is shown. The system 600 may include a cabinet 605, with an x-ray source 630 and an x-ray detector 635. The x-ray detector 635 may be disposed below the x-ray source 630. In one example implementation, the size of the cabinet 605 is approximately 32"×25".

In an embodiment, as shown in FIG. 6A, the x-ray source 630 is disposed at a top of the cabinet 605, and the x-ray detector 635 is disposed at a base 560 of the cabinet. Similarly to system 500, a specimen drawer 645 may be included in the cabinet 605. The specimen drawer 645 may be disposed between the x-ray source 630 and the x-ray detector 635. In this embodiment, both the x-ray source 630 and the x-ray detector 635 are rotated around the specimen drawer 645. The specimen drawer 645 and/or the specimen container can be configured to move from Position A to Position B to Position C. The specimen container is placed at the center of the vertical axis 540, proximate the x-ray detector in position A. In one example, an arm assembly 690 may be connected to the cabinet, via an articulating arm. The arm assembly may include a "C" shaped arm, which includes the x-ray source 630 and the x-ray detector 635 placed opposing the x-ray source 630 that travels along the "C" shaped arm from position A to position B. The x-ray source 630 is can then be rotated into any number of positions and angles along the path of the C shaped arm. The rotation point of the arm assembly could be located closer to the detector to counter balance the weight of the detector in comparison to the lighter weight of the x-ray source.

The x-ray source 630 and the x-ray detector 635 can be connected to the controller for control the movement of the x-ray source 630 and the x-ray detector 635. In one example implementation the x-ray source 630 and the x-ray detector 635 can be connected to the controller via the arm assembly 690. A signal from the controller can be translated into instructions to move the arm assembly which then translated the motion to the x-ray detector and the x-ray source.

In example use of the system 600, in Position A, the x-ray source 630 and the x-ray detector 635 with respect to the vertical axis 540, are not moved and remains at 0 deg. The x-ray source is then activated and an image is taken. The x-ray source 630 and the x-ray detector 635 are then moved together into Position B, at 90 deg. with respect to the vertical axis 540, where the x-ray source is activated.

Inventors appreciate that imaging in position B could potentially result in magnification artifacts. In order to reduce artifacts, the specimen container 685 could be moved horizontally towards the x-ray detector 635 to be placed closer to the x-ray detector 635. In one embodiment, the specimen drawer 645 may include mechanical assembly that allows for the specimen drawer to be moved to the position closer to the x-ray detector 635 in Position C. In one embodiment, a conveyor belt would translate the specimen container linearly in the horizontal direction. In another embodiment, a central platform having a horizontal section where the container is placed and a vertical arm could be translated into movement along the horizontal direction. In this embodiment, a first image is taken at Position A and a second image is taken at Position C.

Referring now to FIGS. 6D and 6E, a radiography scanning system 600d according to another embodiment of the present invention is shown. In one example implementation, the size of the cabinet is approximately 31"×25". In example use of the system 600d, as shown in FIGS. 6D and 6E, in Position A, the x-ray source 630 and the x-ray detector 635 are both rotated to be placed at a first angle with respect to the vertical axis 540. The x-ray source is then activated and an image is taken. The x-ray source 630 and the x-ray detector 635 are then moved together into Position B, at a second angle with respect to the vertical axis 540, where the x-ray source is again activated. Similar to FIG. 6C, to reduce artifacts, the specimen container 685 and the specimen drawer could be moved as close as possible to the x-ray detector 635. In one embodiment, the specimen drawer 645 may include mechanical assembly that allows for the specimen drawer to be moved to the position closer to the x-ray detector 635. It is noted that the specimen drawer 645 may be smaller and span less than the entire width of the cabinet in order to allow more room for the detector to be rotated into position B. For example, the mechanical assembly may be attached to the back of the cabinet. The images taken at position A and position B are then stored and processed and are then both displayed to a user.

Referring now to FIGS. 6F and 6G, a radiography scanning system 600f according to another embodiment of the present invention is shown. In this embodiment, there are two x-ray sources 630a and 630b, where 630a is disposed at a top of the cabinet 605, and 630b is disposed at the side of the cabinet 605 along the horizontal axis 640. Two x-ray detectors 635a and 635b are disposed in the cabinet 605. The x-ray detectors 635a is disposed at a base of the cabinet and the x-ray detector 635b is disposed at the side of the cabinet 605 opposite the x-ray source 630b, along the horizontal axis 640. The specimen drawer 645 is included in the cabinet 605 and is disposed between both the x-ray sources 630a and b and the x-ray detectors 635a and b. At Position A, shown in FIG. 6F, the specimen drawer 645 is disposed proximate the x-ray detector 635a. In this embodiment, the x-ray sources 630a, b and the x-ray detectors 635a,b are stationary. In Position B, the specimen container and the specimen drawer 645 move horizontally, as described with reference to FIG. 6C, so that the specimen container is positioned proximate the x-ray detector 635b.

In example use of the system 600f, as shown in FIGS. 6F and 6G, in Position A, the x-ray source 630 and the x-ray detector 635 are stationary and the specimen drawer is moved to be proximate to the x-ray detector 635a The x-ray source 630a and x-ray detector 630b are then activated and an image is taken. The specimen drawer is then moved along the vertical axis to position B, the specimen container 685 is moved to be proximate to the x-ray detector 630b. The x-ray source 630b and x-ray detector 630b are then activated. The images taken at position A and position B are stored and processed and displayed on a display.

Note that with reference to FIGS. 5C-D and 6A-G, although the x-ray sources and detectors may be shown outside of the cabinet, those elements are located within the cabinet.

Figure 7:
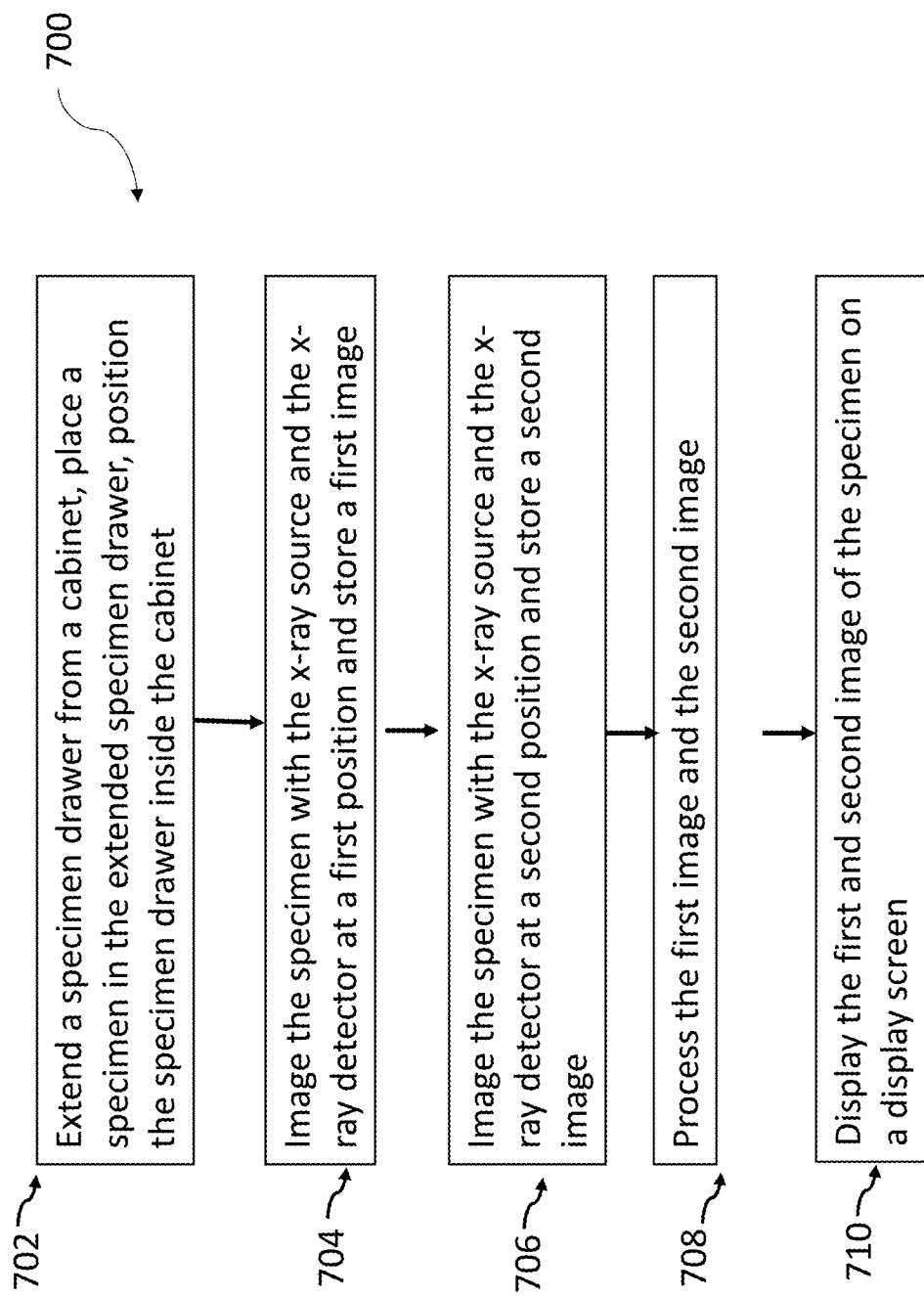
FIG. 7 illustrates a flow diagram of a method of scanning a specimen in a specimen radiography system according to another embodiment of the present invention.

Referring now to FIG. 7, a flow diagram 700 of a method of scanning a specimen in a specimen radiography system is shown. At step 702, the specimen drawer is extended from a cabinet of the specimen radiography system. The controller may direct specimen drawer, from a program stored in a memory of the controller, from user input, or a combination thereof. At step 702, the user may place the specimen in the extended specimen drawer, and the drawer is positioned is positioned along a vertical axis in the cabinet. At step 704, the specimen is imaged with an x-ray source and an x-ray detector at a first position. The first position could be the Position A in any of the FIGS. 5C, 6A, 6D, and 6F described above. The first position could include rotating or moving the x-ray source, the specimen drawer, the specimen container, the x-ray detector or a combination thereof as described above. The image received at the first position is stored as a first image. At step 706, the specimen is imaged with an x-ray source and an x-ray detector at a second position. The second position could be the Position B or C in any of the FIGS. 5D, 6B, 6C, 6E, and 6G described above. The second position could include rotating or moving the x-ray source, the specimen drawer, the specimen container, the x-ray detector, or a combination thereof as described above. The image received at the second position is stored as a second image. At step 708, the first and the second image of the specimen are processed. At step 710, the first and the second image of the specimen are shown on a display screen.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A specimen radiography system comprising:
   a controller; and
   a cabinet comprising:
      an x-ray source,
      an x-ray detector, and
      a specimen drawer, disposed between the x-ray source and the x-ray detector, the specimen drawer being operably connected to the controller, the controller controlling a position of the specimen drawer along a vertical axis between the x-ray source and the x-ray detector, wherein the specimen drawer is extendable from the cabinet for receiving a specimen.

2. The specimen radiography system according to claim 1, wherein the specimen drawer is rotatable.

3. The specimen radiography system according to claim 1, wherein the specimen drawer is configured to extend from the cabinet at an ergonomic position relative to a user.

4. The specimen radiography system according to claim 1, wherein the cabinet is portable.

5. The specimen radiography system according to claim 1, wherein the specimen drawer comprises a generally radiolucent material.

6. The specimen radiography system according to claim 1, wherein the x-ray source is disposed above the x-ray detector along the vertical axis.

7. The specimen radiography system according to claim 1, wherein the x-ray detector is disposed above the x-ray source along the vertical axis.

8. The specimen radiography system according to claim 1, wherein the controller is configured to align the specimen drawer with a focal point of the x-ray source.

9. The specimen radiography system according to claim 1, further comprising a user interface, and wherein the controller is configured to at least one of automatically position and rotate the specimen drawer in response to an input received by the user interface.

10. The specimen radiography system according to claim 1, wherein the specimen drawer is configured to be extendable from and retractable within the cabinet.

11. A method of scanning a specimen in a specimen radiography system including a controller, the method comprising:
   receiving the specimen within a specimen drawer extended from a cabinet;
   positioning, using the controller, the specimen drawer along a vertical axis in the cabinet, the specimen drawer movable between an x-ray source and an x-ray detector;
   imaging the specimen with the x-ray source and the x-ray detector; and
   displaying a specimen image on a display screen.

12. The method according to claim 11, wherein positioning the specimen drawer along a vertical axis in the cabinet comprises at least one of:
   disposing the x-ray source above the specimen drawer, or
   disposing the x-ray detector above the specimen drawer.

13. The method according to claim 11, further comprising receiving information via a user interface to direct the specimen drawer along the vertical axis in the cabinet between the x-ray source and the x-ray detector within the cabinet.

14. The method according to claim 11, further comprising positioning the specimen drawer along the vertical axis in the cabinet between the x-ray source and the x-ray detector in response to a magnification setting received by a user interface.

15. The method according to claim 11, further comprising rotating the specimen drawer in response to a position setting received by a user interface.

16. The method according to claim 11, wherein positioning the specimen drawer along a vertical axis in the cabinet comprises aligning the specimen drawer with a focal point of the x-ray source.

17. A specimen radiography system comprising:
a controller; and
a cabinet comprising:
an x-ray source,
an x-ray detector, and
a specimen drawer, disposed between the x-ray source and the x-ray detector, the specimen drawer being operably connected to the controller, the controller controlling a position of the specimen drawer along a vertical axis between the x-ray source and the x-ray detector, wherein the specimen drawer is rotatable.

18. The specimen radiography system according to claim 17, wherein the specimen drawer comprises a generally radiolucent material.

19. The specimen radiography system according to claim 17, wherein the controller is configured to align the specimen drawer with a focal point of the x-ray source.

20. The specimen radiography system according to claim 17, further comprising a user interface, and wherein the controller is configured to at least one of automatically position and rotate the specimen drawer in response to an input received by the user interface.

* * * * *